United States Patent [19]

Bangs

[11] Patent Number: 5,234,454
[45] Date of Patent: Aug. 10, 1993

[54] PERCUTANEOUS INTRAGASTRIC BALLOON CATHETER AND METHOD FOR CONTROLLING BODY WEIGHT THEREWITH

[75] Inventor: Roger G. Bangs, West Lafeyette, Ind.

[73] Assignee: Akron City Hospital, Akron, Ohio

[21] Appl. No.: 740,331

[22] Filed: Aug. 5, 1991

[51] Int. Cl.⁵ ......................................... A61M 25/10
[52] U.S. Cl. ....................................... 606/191; 604/96
[58] Field of Search .......................... 604/220, 96–101; 606/191–198

[56] References Cited

U.S. PATENT DOCUMENTS

| | | | |
|---|---|---|---|
| 2,687,131 | 8/1954 | Raiche | 128/349 |
| 3,952,742 | 4/1976 | Taylor | 128/172.1 |
| 4,057,065 | 11/1977 | Thow | 128/348 |
| 4,133,315 | 1/1979 | Berman et al. | 128/303 |
| 4,246,893 | 1/1981 | Berson | 128/1 |
| 4,315,513 | 2/1982 | Nawash et al. | 128/348 |
| 4,368,739 | 1/1983 | Nelson, Jr. | 604/54 |
| 4,393,873 | 7/1983 | Nawash et al. | 604/151 |
| 4,416,267 | 11/1983 | Garren et al. | 128/1 |
| 4,464,175 | 8/1984 | Altman et al. | 604/99 |
| 4,485,805 | 12/1984 | Foster, Jr. | 128/1 |
| 4,601,713 | 7/1986 | Fuqua | 604/280 |
| 4,624,657 | 11/1986 | Gould et al. | 604/103 |
| 4,648,892 | 3/1987 | Kittrell et al. | 65/4.21 |
| 4,666,433 | 5/1987 | Parks | 604/178 |
| 4,669,467 | 6/1987 | Willett et al. | 128/303 |
| 4,676,778 | 6/1987 | Nelson, Jr. | 604/45 |
| 4,685,901 | 9/1987 | Parks | 604/96 |
| 4,694,827 | 9/1987 | Weiner et al. | 128/303 |
| 4,701,163 | 10/1987 | Parks | 604/178 |
| 4,705,040 | 11/1987 | Mueller et al. | 128/334 |
| 4,710,181 | 12/1987 | Fuqua | 604/280 |
| 4,718,417 | 1/1988 | Kittrell et al. | 128/303 |
| 4,738,666 | 4/1988 | Fuqua | 604/280 |
| 4,798,592 | 1/1989 | Parks | 604/49 |
| 4,861,334 | 8/1989 | Nawaz | 604/49 |
| 4,899,747 | 2/1990 | Garren et al. | 606/192 |
| 4,905,667 | 3/1990 | Foerster et al. | 128/4 |
| 4,913,142 | 4/1990 | Kittrell et al. | 606/7 |
| 4,932,956 | 6/1990 | Reddy et al. | 606/192 |
| 5,071,405 | 12/1991 | Piontek et al. | 604/96 |

OTHER PUBLICATIONS

Brown et al.—"Controlled Percutaneous Gastrostomy: Nylon T-Fastener For Fixation of the Anterior Gastric Wall" Radiology, vol. 15B, No. 2, Dec. 1986.

D. Durrans et al–"Intragastric Balloons" *Journal of the Royal College of Surgeons of Edinburgh,* vol. 30, No. 6, Dec., 1985.

(List continued on next page.)

*Primary Examiner*—C. Fred Rosenbaum
*Assistant Examiner*—Manuel Mendez
*Attorney, Agent, or Firm*—Renner, Kenner, Greive, Bobak, Taylor & Weber

[57] ABSTRACT

A method for controlling the body weight of a patient employs a percutaneous intragastric balloon catheter (10). The method comprises the first steps of inserting a percutaneous intragastric balloon catheter (10) into the stomach of the patient through a gastrostomy tract. The intragastric balloon catheter (10), in turn, comprises elongated shaft means (11) having first (12) and second (13) ends, a first inflatable balloon (14) carried proximal to the first end; a second inflatable balloon (15) carried proximal to the first inflatable balloon, the second balloon having a lesser inflated volume than the first balloon; first and second inflation lumens (18, 20); first and second inflation ports (22, 23) communicating respectively with the first and second inflation lumens and the first and second balloons, which ports are carried by the second end (13); a drainage lumen (16) passing between said first and second ends. The method continues by inflating the first and second balloons within the patient, partially filling the stomach to provide satiety. The intragastric balloon catheter employed is also deemed to be novel.

4 Claims, 4 Drawing Sheets

Granström and Backman–"Stomach Distension in Extremely Obese and in Normal Subjects" *Acta Chir Scand,* 151:367–370, 1985.

Abstract for the Garren Gastric Bubble–*Gastrointestinal Endoscopy,* 31:162, 1985.

Brown et al–"Controlled Percutaneous Gastrostomy: Nylon T-Fastener for Fixation of the Anterior Gastric Wall" *Radiology,* vol. 158, No. 2, Dec., 1986.

Boyle et al–"Small Intestinal Obstruction Secondary to Obturation by a Garren Gastric Bubble" *The American Journal of Gastroenterology,* Jan., 1987.

McFarland et al–"The Intragastric Balloon: A Novel Idea Proved Ineffective" *British Journal of Surgery,* vol. 74, 137–139, Feb., 1987.

Kirby et al–"Incomplete Small Bowel Obstruction by the Garren-Edwards Gastric Bubble Necessitating Surgical Intervention", Mar. 1987.

Yang et al–"Use of Intragastric Balloons for Weight Reduction" *The American Journal of Surgery,* vol. 153, Mar. 1987.

Schapiro et al–"Obesity and the Gastric Balloon: A Comprehensive Workshop" *Gastrointestinal Endoscopy,* Apr. 1987.

M. Mellows and S. Brozinsky–Letters to the Editor *Gastrointestinal Endoscopy,* vol. 33, No. 5, May 1987.

Kartsonis et al–Letters to the Editor *G. E.,* vol. 33, No. 5, May 1987.

M. Fedotin and B. W. Ginsberg–"Partial Development of the Garren Gastric Bubble: A New Complication" *The American Journal of Gastroenterology,* May 1987.

Lieber et al–Temporary Intervention: Dental Splinting and the Intragastric Bubble", Sep. 1987.

Lindor et al–"Intragastric Balloons in Comparison with Standard Therapy for Obesity-A Randomized, Double Blind Trial" *Mayo Clin. Proc.,* Nov. 1987.

Durrans et al–Abstract on the Taylor Intragastric Balloon–*The American Journal of Gastroenterology,* 82:943, 1987.

Benjamin et al–Abstract entitled "A Double-Blind Cross Over Study of the Garren-Edwards Anti-Obesity Bubble", *Gastrointestinal Endoscopy,* 82:168, 1987.

Chapman et al–Abstract entitled "The Effectiveness of the Gastric Bubble in the Treatment of Morbid Obesity" *Gastrointestinal Endoscopy,* 33:170, 1987.

Farivar et al–Abstract entitled "Garren-Edwards Gastric Bubble for Obese Patients" *Gastrointestinal Endoscopy,* 33:170, 1987.

Frank et al–Abstract for Weight Loss Using a Gastric Balloon *Gastrointestinal Endoscopy,* 33:170, 1987.

Gaeke et al–Abstract for Weight Loss Using a Gastric Balloon *Gastrointestinal Endoscopy,* 33:171, 1987.

Good et al–Abstract for Weight Loss Using a Gastric Balloon *Gastrointestinal Endoscopy,* 33:171, 1987.

Hogan–Abstract–*Gastrointestinal Endoscopy,* 33:172.

Brown et al–"The Effect of an Intragastric Balloon on Weight Loss, Gastric Acid Secretion and Serum Peptide Levels" *The American Surgeon,* Feb. 1988.

Dagradi and Lee–Letter to the Editor–*Gastrointestinal Endoscopy,* Mar. 1988.

Dr. John Hamilton–"Gastric Balloons to Treat Obesity", May 1988.

Malcolm et al–"Update on the Management of Obesity" *Southern Medical Journal,* May 1988.

Editorial–"Intragastric Devices for Weight Loss: Fact or Fancy?" *The American Journal of Gastroenterology,* May 1988.

Stanley Benjamin–"Small Bowel Obstruction and the Garren-Edwards ® Gastric Bubble: An Iatrogenic Bezoar", Jun. 1988.

John Kral–"Gastric Balloon: A Plea for Sanity in the Midst of Balloonacy" *Gastroenterology*, Jul. 1988.

Gary Levine–"Intragastric Balloons: An Unfulfilled Promise" *Annals of Internal Medicine*, Sep. 1988.

Editorial–"Who Needs an Intragastric Balloon for Weight Reduction" *The Lancet*, Sep. 17, 1988.

Barkin et al–"Effects of Gastric Bubble Implant on Weight Change With & Without Compliance of Behavior Modification Program" *The American Journal of Gastroenterology*, Sep. 1988.

Barkin et al–"The Effects of Morbid Obesity and the Garren-Edwards Gastric Bubble on Soplid Phase Gastric Emptying" *The American Journal of Gastroenterology*, Dec. 1988.

Allan Geliebter–"Gastric Distension and Gastric Capacity in Relation to Food Intake in Humans" *Physiology & Behavior*, 1988.

Garren et al–Abstract–Study Using the Garren Edwards Gastric Bubble with Behavior Modification and Nutritional Counseling *Gastrointestinal Endoscopy*, 1988.

Holmes et al–"An Analytic Review of Current Therapies for Obesity" *The Journal of Family Practice*, 1989.

Mathus-Vliegen et al–"Intragastric Balloons for Morbid Obesity: Results, Patient Tolerance and Balloon Life Span", 1989.

Durrans et al–"Comparison of Weight Loss with Short Term Dietary and Intragastric Balloon Treatment", 1989.

L. Elsborg–"A Novel Device for Removal of the Gastric Remnant after Intragastric Balloon Implantation for Obesity", Sep. 1989.

News Article–"Gastric Balloon for Morbidly Obese Does Not Greatly Decrease Weight", based on report in *Gastrointestinal Endoscopy* and an interview with Dr. Reed Hogan, Jan. 1990.

Kirby et al–"A Prospective Assessment of the Garren–Edwards Gastric Bubble and Bariatric Surgery in the Treatment of Morbid Obesity".

Vosudeva et al–"Taylor Intragastric Balloon", Dec. 1990.

Weiner–"Taylor Intragastric Balloon", Dec. 1990.

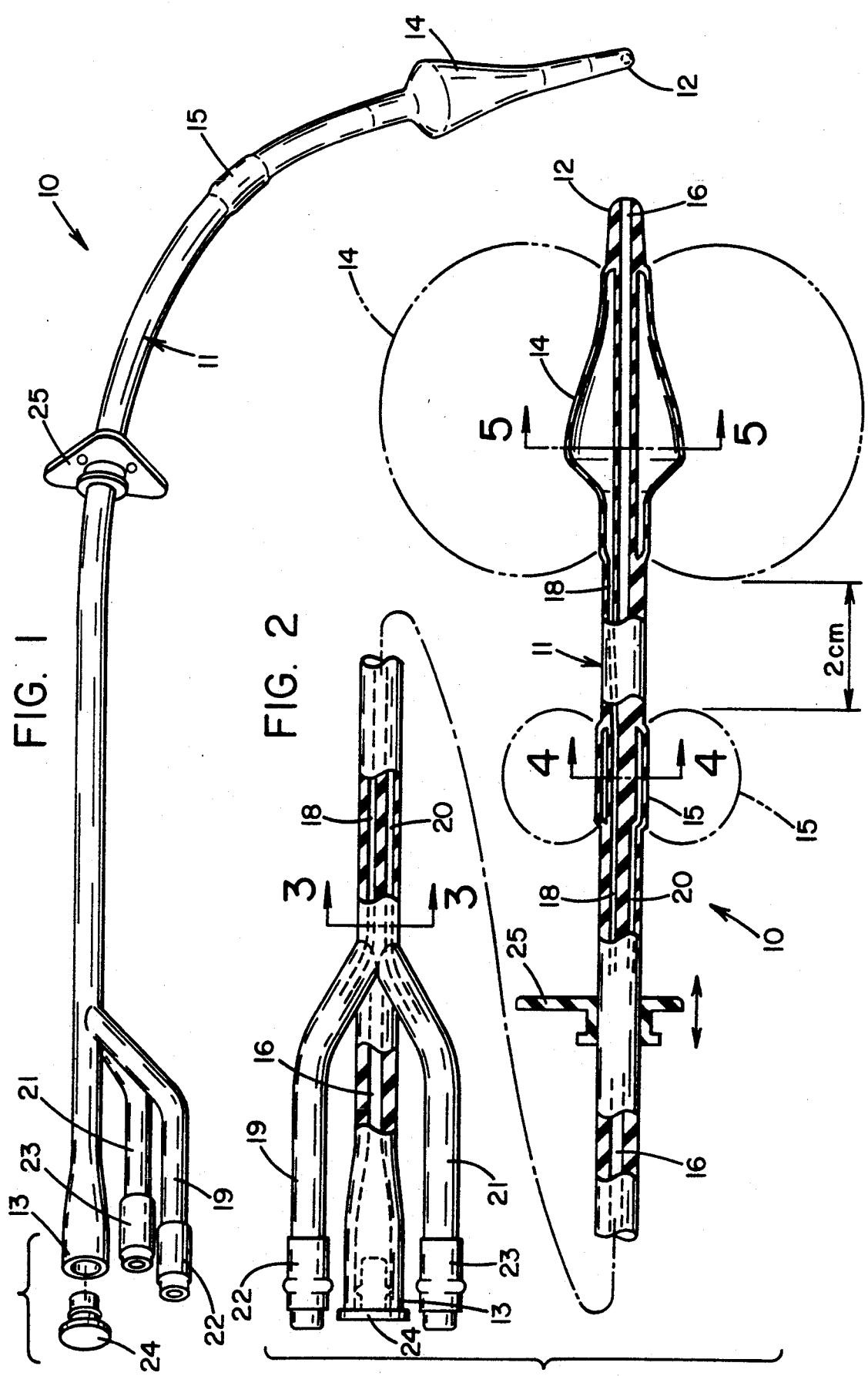

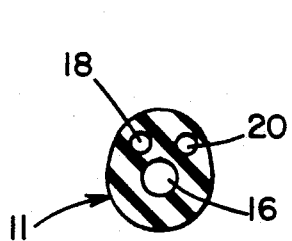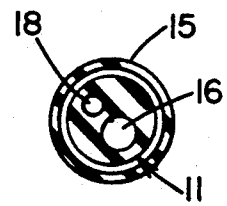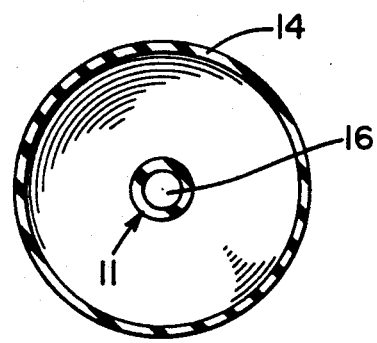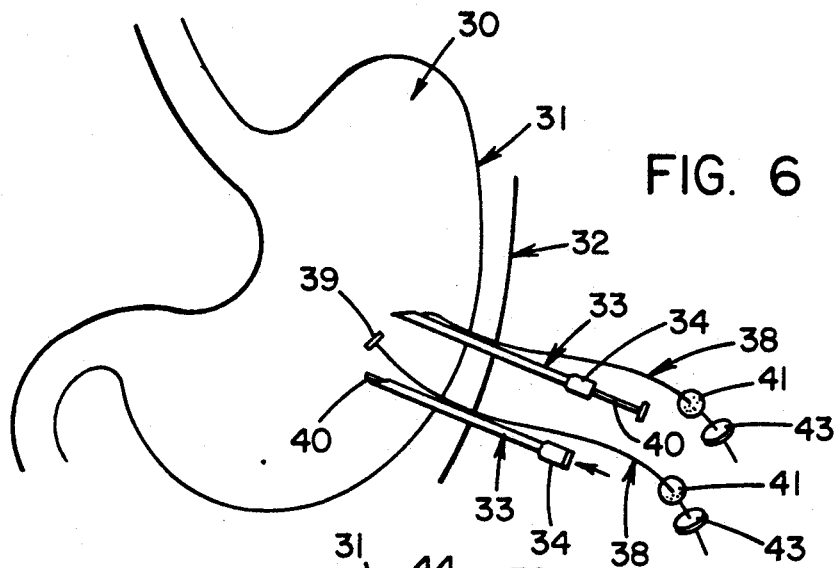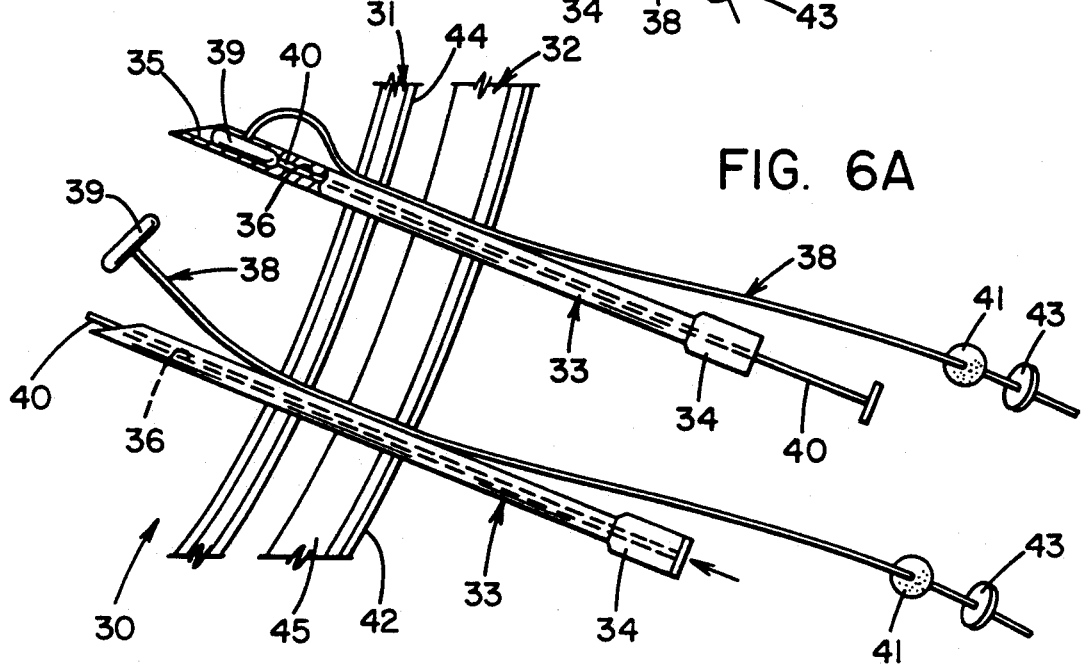

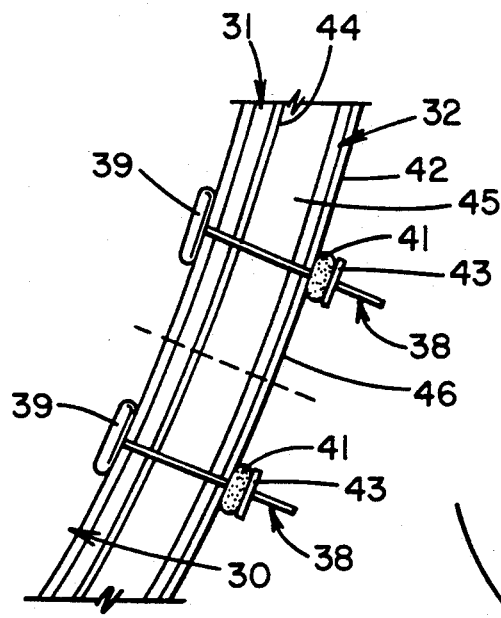
FIG. 6B
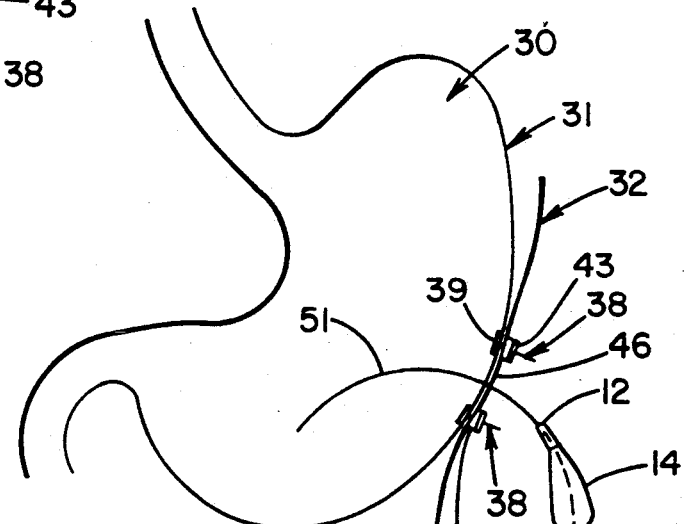
FIG. 7
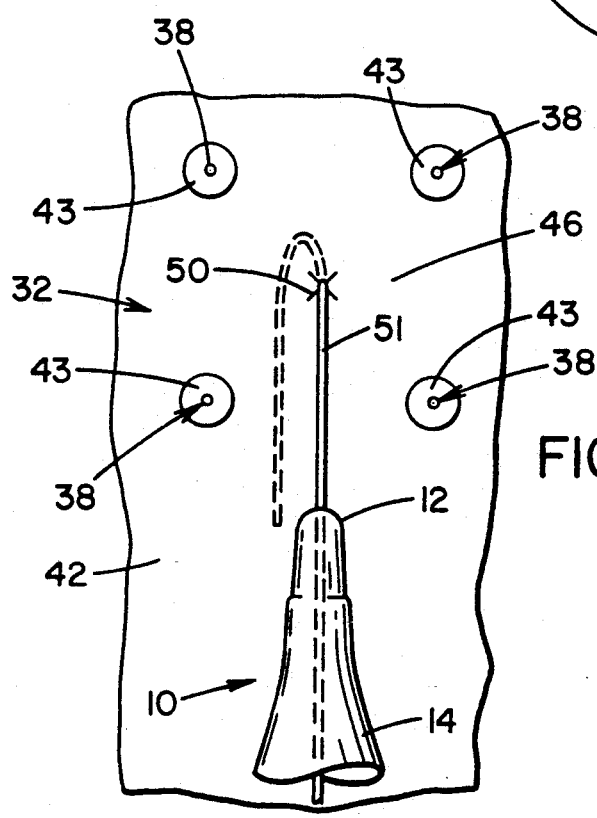
FIG. 7A
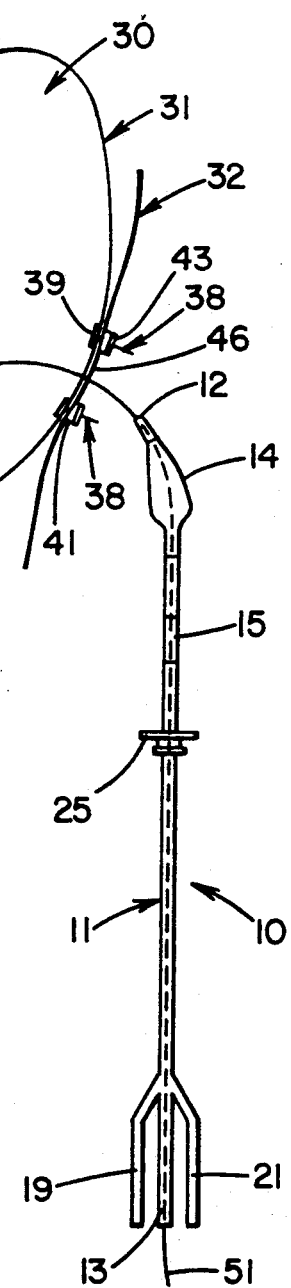

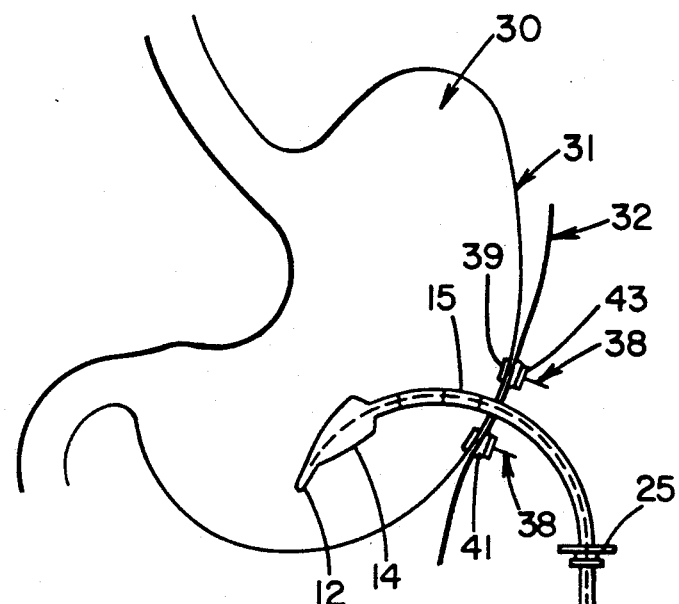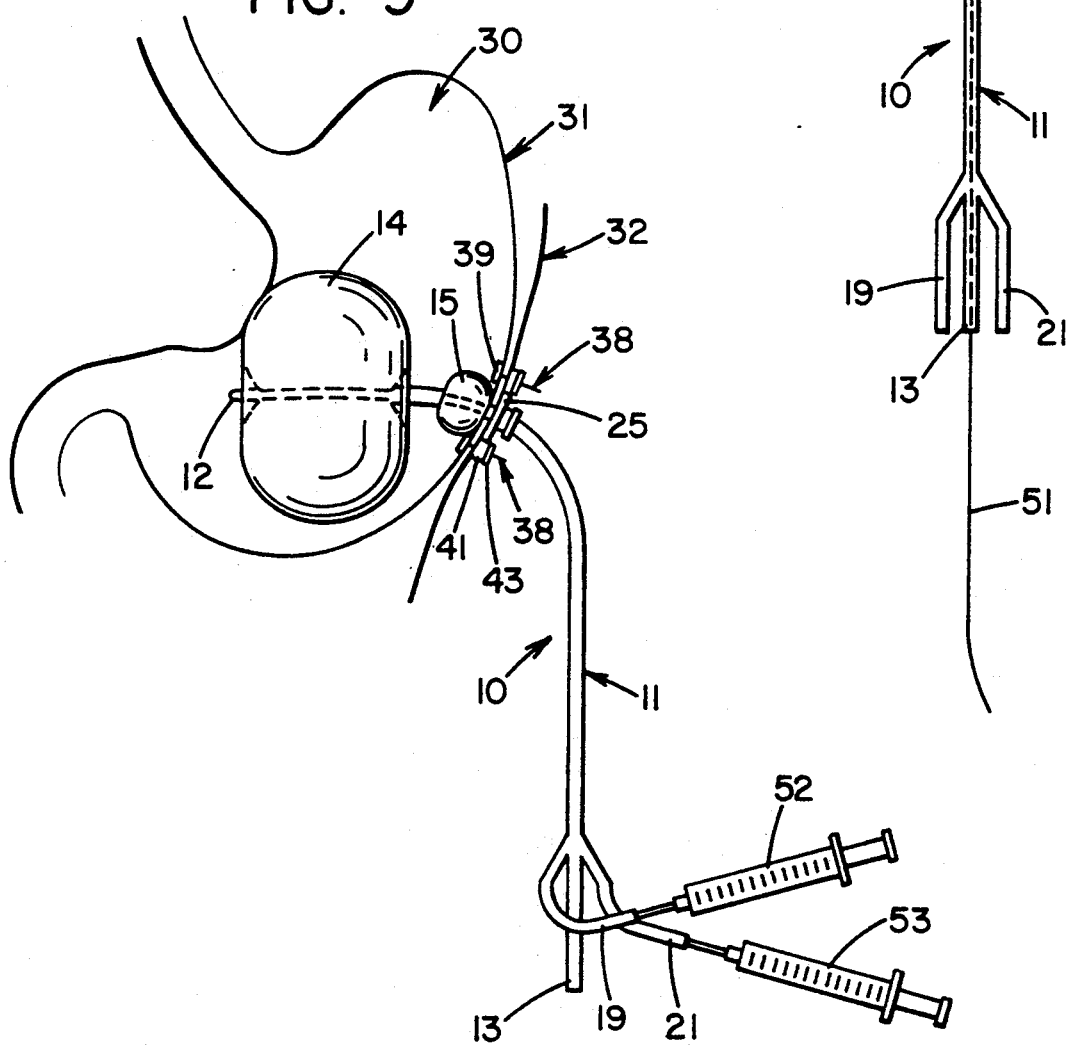

PERCUTANEOUS INTRAGASTRIC BALLOON CATHETER AND METHOD FOR CONTROLLING BODY WEIGHT THEREWITH

TECHNICAL FIELD

This invention relates to gastrostomy catheters for use in the management of weight control. More particularly, the invention relates to balloon catheters positioned in the stomach to provide satiety. Specifically, the invention relates to percutaneous intragastric balloon catheters for use as adjuncts to weight control in obesity. A method for controlling the body weight of patients utilizing the catheter is also provided.

BACKGROUND ART

Obesity is a major medical problem affecting millions of people worldwide. In addition to the psychosocial stigmas associated with the condition or disease, many medical problems may develop. Hypertension, heart disease, diabetes, hyperlipidemia, degenerative arthritis and certain types of cancer are more common among overweight individuals. For those persons more than forty-five kilograms overweight, the risk of sudden premature death is twelve times higher than normal. Weight loss often results in a significant reduction in risk of these associated problems.

The recommended methods for weight loss are dietary restriction and behavioral modification. However, many persons are unable to achieve significant or sustained results using these methods. Thus, these individuals have turned to other methods of weight loss, including the use of surgical adjuncts to weight control.

In the past, several surgical adjuncts to weight loss have been proposed. Two of those adjuncts are the jejunoileal bypass which although successful, has been abandoned due to high morbidity and gastric stapling which has evolved to the presently successful vertical banded gastroplasty, but which also has significant morbidity.

Another surgical adjunct is described in U.S. Pat. No. 4,246,893. An inflatable balloon is implanted in the abdominal cavity of the body near the stomach. The inflatable gastric device may be employed by inserting a hypodermic needle in an adjustment port located just under the patient's skin. A passage between the adjustment port and balloon permits a gas or fluid to be passed to the balloon, thereby expanding it, and consequently, compress the stomach, reducing its capacity.

Also developed is the intragastric balloon of Garren et al which is disclosed in U.S. Pat. Nos. 4,416,267 and 4,899,747 was shown to be a possibly efficacious remedy for weight control, although random trials have shown no definite increase in weight loss over behavioral modification alone. It is believed that the failure to show any significant increased weight loss may be caused by a high incidence of spontaneous balloon deflation of eighty percent (80%) during the investigation period. Such a high occurrence of balloon deflation would certainly have reduced the balloon's effectiveness. Nevertheless, nearly eighty percent (80%) of the tested patients did report early satiety.

The Garren-Edwards balloon is fully described and explained in several *Gastrointestinal Endoscopy* publications which are incorporated by reference herein. Specifically, the balloon is a cylindrical bubble of polyurethane inflated with 200 to 220 cubic centimeters of air. The bubble is discharged into the stomach through a large orogastric introducer tube and once in place, the device provides satiety. However, spontaneous deflation of the bubble is prevalent and passage of the deflated device through the pylorus often results in small bowel obstruction which requires surgery. To reduce the complications associated with spontaneous deflation, retrieval of the device was recommended every three (3) months. This requires endoscopic removal and reinsertion of the device if indicated.

A similar device for weight loss is set forth in U.S. Pat. No. 4,485,805 wherein a free-floating, intragastric balloon is placed in the stomach but may be retrieved by endoscopy by a withdrawal loop connected to the balloon. Both the Garrens method and this method (Foster, Jr.) rely greatly on endoscopy which is not only expensive, but also has given rise to complications such as pharyngeal and esophageal perforation and aspiration from its use during deployment and retrieval of the device. Furthermore, the balloon edges and cylindrical shape of the device are believed to have contributed to gastric ulceration or mucosal erosion in some patients. A later-developed smooth, silicone balloon has not been associated with severe gastric mucosal damage and has resulted in increased weight loss.

An even more complex weight loss device is described in U.S. Pat. No. 4,133,315 where the endoscopy tube remains attached to the balloon in the stomach to provide satiety. While this method basically assures retrieval of the balloon upon deflation, the extreme morbidity and discomfort with this method should be selfevident.

Catheters are well known in the medical art, and are commonly used as providing nourishment and for gastrostomy tubes for the purpose of lavaging a patient's stomach. Such gastrostomy devices have been the subject of a number of patents, including U.S. Pat. Nos. 4,315,513 and 4,666,433. It is also known to provide an inflatable balloon as part of the tube so as to hold the tube in place while feeding or lavaging. U.S. Pat. Nos. 4,624,657 and 4,861,334 are just two examples of this. Furthermore, U.S. Pat. No. 2,687,131 provides a catheter having a longitudinal drainage channel and drainage eyes, and inflatable balloon being positioned adjacent the drainage eyes. A second balloon unit is slidably mounted on the tube and is slidably adjustable in holding the tube in place. Nevertheless, the use of catheters for the deployment and retrieval of intragastric balloons has not been discussed in the art pertaining to the intragastric balloon or in the catheter art.

Finally, it is noted that the use of two balloons within a catheter is known in the art. Specifically, U.S. Pat. No. 4,057,065 provides a gastrointestinal tube having an inflatable balloon within the stomach to decompress it and also to provide a seal in the stomach so that any gastric fluids do not spill into the abdominal cavity. A second inflatable balloon is provided at the distal end of the tube which is threaded through the pyloris, jejunum and ligament of Trietz and into the small intestine where it may be inflated to provide both intestinal stent plication and gastric or intestinal decompression.

Notwithstanding the above-described art, the need still exists for a percutaneous intragastric balloon catheter which will provide satiety to a patient without significant risk of morbidity. The need also exists for an intragastric balloon catheter which is easily retrieved and replaced without endoscopy. Furthermore, the need exists for such a balloon to be smooth and have a low ulceration or erosion potential. Even further, the balloon should provide satiety without the risk of obstructing the small intestine upon spontaneous deflation. The need additionally exists for a balloon adjustable in size so as to accommodate individually the volume desired by each patient.

SUMMARY OF THE INVENTION

It is therefore, a primary object of the present invention to provide a percutaneous intragastric balloon catheter for use as an adjunct to weight loss.

It is another object of the present invention to provide a percutaneous intragastric balloon catheter, as above which is easily retrieved and replaced without endoscopy.

It is a further object of the present invention to provide a percutaneous intragastric balloon catheter, as above, which provides satiety to patients.

It is yet another object of the present invention to provide a percutaneous intragastric balloon catheter, as above, which has a low ulceration and erosion potential.

It is yet a further object of the present invention to provide a percutaneous intragastric balloon catheter, as above, having a low risk of small bowel obstruction.

It is still another object of the present invention to provide a method for controlling the body weight of an obese patient using a percutaneous intragastric balloon catheter.

These and other objects, together with the advantageous thereof over the existing prior art forms and known methods, which shall become apparent from the specification which follows, are accomplished by the invention as hereinafter described and claimed.

In general, the present invention provides a method for controlling the body weight of a patient. It comprises the first step of inserting a percutaneous intragastric balloon catheter into the stomach of the patient through a gastrostomy tract, which intragastric balloon catheter comprises elongated shaft means having first and second ends; a first inflatable balloon carried proximal to the first end and a second inflatable balloon carried proximal to the first inflatable balloon, the second balloon having a lesser inflated volume than the first balloon; first and second inflation lumens; first and second inflation ports communicating respectively with the first and second inflation lumens and the first and second balloons, which ports are carried by the second end; and a drainage lumen passing between the first and second ends. The method continues by inflating the first and second balloons within the patient, partially filling the stomach to provide satiety.

The present invention also provides a percutaneous intragastric balloon catheter which comprises elongated shaft means having a first and second ends; a first inflatable balloon carried proximal to the first and; a second inflatable balloon carried proximal to the first inflatable balloon, the second balloon having a lesser inflated volume than the first balloon; first and second inflation lumens; first and second inflation ports communicating respectively with the first and second inflation lumens and the first and second balloons, which ports are carried by the second end; and a drainage lumen passing between the first and second ends.

BRIEF DESCRIPTION OF THE DRAWINGS

FIG. 1 is a perspective view of the percutaneous intragastric balloon catheter of the present invention;

FIG. 2 is an enlarged bottom plan elevation of the percutaneous intragastric balloon catheter of the present invention, partially in section and depicting the two balloons in their inflated position;

FIG. 3 is a further enlarged section, taken substantially along lines 3—3 of FIG. 2, depicting the lumens in the catheter;

FIG. 4 is a section, taken substantially along lines 4—4 of FIG. 2, depicting the lumens in the catheter and the smaller of the two balloons;

FIG. 5 is a section, taken substantially along lines 5—5 of FIG. 2, depicting the lumens in the catheter and the larger of the two balloons;

FIG. 6 schematically depicts the stomach and abdominal wall of a patient and a technique for providing a gastrostomy tract;

FIGS. 6A–6B are enlarged schematic views, similar to FIG. 6, depicting the sequential steps of providing a gastrostomy tract;

FIG. 7 schematically depicts the stomach and abdominal wall of a patient and the insertion of the catheter through the gastrostomy tract;

FIG. 7A is an enlarged, fragmentary, frontal elevation depicting the insertion of the catheter through the gastrostomy tract;

FIG. 8 schematically depicts the stomach and abdominal wall of a patient and the emplacement of the catheter in the stomach; and FIG. 9 schematically depicts the stomach and abdominal wall of a patient and the inflation of the catheter in the stomach.

PREFERRED EMBODIMENT FOR CARRYING OUT THE INVENTION

The percutaneous intragastric catheter of the present invention is depicted generally by the numeral 10. It comprises an elongate flexible shaft 11 having a first, or distal end 12 and a second, or proximal end 13. A first, or distal inflatable balloon 14 is provided near the distal end 12 and a second, or proximal inflatable balloon 15 is provided proximal thereto. The catheter 10 is a 20 French latex catheter, manufactured via conventional methods for catheter production, which are employed to provide the inflatable balloons 14 and 15 on shaft 11.

With reference to FIG. 2, the shaft 11 carries a central drainage lumen 16 which passes between the distal and proximal ends. A first inflation lumen 18 is provided in the shaft 11 which communicates with the first balloon 14 and an inflation arm 19 and in similar fashion, a second inflation lumen 20 is provided in the shaft 11 which communicates with the second balloon 15 and an inflation arm 21, both arms being carried near the proximal end 13. Arms 19 and 21 are provided with conventional valves 22 and 23, respectively, which allow the balloons, 14 and 15 to be inflated and deflated separately with a hypodermic syringe, as is known in the art. Hence, further discussion of these components is not necessary to the understanding of the present invention. The catheter 10 also carries a cap 24 at the proximal end, to seal the lumen 16, and a slidable anchor 25 along the shaft 11, which will be discussed hereinbelow.

Prior to use, it is necessary to prepare a gastrostomy tract in the patient for insertion of the catheter. A variety of techniques are known for preparing such a tract and thus, the particular technique elected can be one preferred by the physician, it being understood that practice of the present invention is not limited thereto. What is important to the present invention is that the percutaneous intragastric balloon catheter, utilizes a percutaneous route of deployment via a mature gastrostomy that avoids the complications with spontaneous deflation and transesophageal deployment and retrieval that accompany existing techniques for controlling obesity as discussed hereinabove.

One useful technique for preparing a gastrostomy is described in RADIOLOGY, Vol. 158, No. 2, pp 543-545 (1986) entitled "Controlled Percutaneous Gastrostomy: Nylon T-Fastener for Fixation of the Anterior Wall". The authors described a fixation device employing nylon garmet T-fasteners to affix the anterior gastric wall to the abdominal wall for percutaneous gastrostomy which is, in turn, briefly summarized herein. With reference to FIGS. 6, 6A, 6B, 7 and 7A, the technique is illustrated sequentially.

In FIG. 6, the anterior wall 31 of a stomach 30 and the adjacent abdominal wall 32 of a patient are depicted. The walls 32 and 31 are pierced with a needle 33, enlarged in FIG. 6A. Needle 33 provides a proximal hub 34 and a distal slot 35, connected by a lumen 36. An elongated T-fastener or similar device 38 is mounted on the needle 33 by placing the "T" 39 within the distal slot 35. The needle 33 is then inserted through the walls 32 and 31, carrying with it the fastener 38. Once within the stomach, the fastener is released from the needle by means of a stylet 40, a depicted in the lower portion of FIG. 6A, following which the needle is withdrawn. At this point, a cotton pledget 41 is slid along the fastener to engage the exterior surface 42 of the abdominal wall, followed by a brass swedget 43. Both are tightened against the abdominal wall, drawing up the anterior wall exterior 44 of the stomach and fatty layer 45, and then the swedget 43 is held in place with a hemostat.

In order to ensure proper fixation of the fastener 38, the stomach can be initially inflated with air until well distended. Preferably, four fasteners 38 are employed, defining a quadrant are 46 (FIG. 7A). When the correct tension is established with hemostats, the swedgets 43 are crimped with swedging pliers (not shown). The proximal end of the fastener 38 can be cut away and disposed and the anterior wall of the stomach is now snugly affixed to the anterior abdominal wall. Next, an incision or hole 50, is made through the quadrant 46 with an 18 gauge sheath and a heavy duty guide wire 51 is inserted therethrough. Graduated vascular dilators (not shown) are advanced over the guide wire up to about 18 French. At this stage, the catheter 10 is introduced over the guide wire 51 and into the stomach 30 (FIGS. 7 and 7A), following which the wire is removed (FIG. 8).

As the final step for emplacement, the anchor 25 is affixed to the abdominal wall 32 via suturing or other suitable means. A hypodermic syringe 52 is then connected to the arm 19 and distal balloon 14 is inflated to about 200 to 500 cc's, following which a second syringe 53 is connected to the arm 21 and proximal balloon 15 is inflated to about 20 cc's, as depicted in FIG. 9. Generally, there is a space of at least two centimeters between the two balloons to allow some mobility of the large distal balloon 14. The surface of the balloon is smooth to help prevent gastric erosion. Spontaneous deflation or rupture may still occur; however, the catheter is easily withdrawn and exchanged for a new one. The proximal balloon 15 prevents accidental withdrawal of the catheter associated with deflation of the distal balloon. Passage of the balloon distally into the small bowel is avoided because the catheter is anchored to the abdominal wall.

Based upon the foregoing disclosure, it should now be apparent that the use of the catheter described herein will carry out the objects set forth hereinabove. In particular, the catheter and method of the present invention are highly effective as a means for controlling the body weight of a patient by providing satiety. It is, therefore, to be understood that any variations evident fall within the scope of the claimed invention and thus, the selection of specific component elements in the design of the catheter 10 can be determined without departing from the spirit of the invention herein disclosed and described. Thus, the scope of the invention shall include all modifications and variations that may fall within the scope of the attached claims.

What is claimed is:

1. A method for controlling the body weight of a patient comprising the steps of:
   inserting a percutaneous intragastric balloon catheter into the stomach of the patient through a gastrostomy tract;
   said intragastric balloon catheter comprising
       elongated shaft means having first and second ends;
       a first inflatable balloon carried proximal to said first end;
       a second inflatable balloon carried proximal to said first inflatable balloon, said second balloon having a lesser inflated volume than said first balloon;
       first and second inflation lumens;
       first and second inflation ports communicating respectively with said first and second inflation lumens and said first and second balloons, said ports being carried by said second end; and
       a drainage lumen passing between said first and second ends; and
   inflating said first and second balloons within the stomach of the patient, partially filling the stomach, to provide satiety.

2. A method, as set forth in claim 1, including the additional step of allowing said gastrostomy tract to mature for at least four weeks.

3. A method, as set forth in claim 1, including the additional step of anchoring said intragastric balloon catheter outside the body of the patient with external retaining means carried distally of said second end.

4. A method, as set forth in claim 1, further comprising the steps of:
   retrieving said intragastric balloon catheter; and
   replacing said intragastric balloon catheter.

* * * * *